United States Patent
Seibel et al.

(10) Patent No.: US 9,742,993 B2
(45) Date of Patent: Aug. 22, 2017

(54) EXTENDED DEPTH OF FOCUS FOR HIGH-RESOLUTION OPTICAL IMAGE SCANNING

(71) Applicant: University of Washington through its Center for Commercialization, Seattle, WA (US)

(72) Inventors: Eric J. Seibel, Seattle, WA (US); Brian T. Schowengerdt, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 16 days.

(21) Appl. No.: 14/379,270

(22) PCT Filed: Feb. 15, 2013

(86) PCT No.: PCT/US2013/026527
§ 371 (c)(1),
(2) Date: Aug. 15, 2014

(87) PCT Pub. No.: WO2013/123461
PCT Pub. Date: Aug. 22, 2013

(65) Prior Publication Data
US 2015/0009357 A1     Jan. 8, 2015

Related U.S. Application Data

(60) Provisional application No. 61/599,839, filed on Feb. 16, 2012.

(51) Int. Cl.
*H01J 3/14* (2006.01)
*H04N 5/232* (2006.01)
(Continued)

(52) U.S. Cl.
CPC ..... *H04N 5/23235* (2013.01); *A61B 1/00167* (2013.01); *A61B 1/00172* (2013.01);
(Continued)

(58) Field of Classification Search
CPC .......................... G02B 23/243; G02B 23/2469
(Continued)

(56) References Cited

U.S. PATENT DOCUMENTS

| 7,159,782 B2 | 1/2007 | Johnston et al. |
| 7,189,961 B2 | 3/2007 | Johnston et al. |

(Continued)

FOREIGN PATENT DOCUMENTS

| JP | 2004502957 A | 1/2004 |
| JP | 2010158358 A | 7/2010 |

(Continued)

OTHER PUBLICATIONS

Rivera, et al. Multifocal multiphoton endoscope. Opt Lett. Apr. 15, 2012;37(8):1349-1351. doi: 10.1364/OL.37.001349.
(Continued)

*Primary Examiner* — Thanh Luu
(74) *Attorney, Agent, or Firm* — Wilson Sonsini Goodrich & Rosati

(57) ABSTRACT

Methods and systems for acquiring and/or projecting images from and/or to a target area are provided. Such a method or system can includes an optical fiber assembly which may be driven to scan the target area in a scan pattern. The optical fiber assembly may provide multiple effective light sources (e.g., via a plurality of optical fibers) that are axially staggered with respect to an optical system located between the optical fiber and the target area. The optical system may be operable to focus and/or redirect the light from the multiple light sources onto separate focal planes. A composite image may be generated based on light reflected from (Continued)

and/or projected onto the separate focal planes. The composite image may have an extended depth of focus or field spanning over a distance between the separate focal planes while maintaining or improving image resolution.

20 Claims, 12 Drawing Sheets

(51) Int. Cl.
    *A61B 1/07*     (2006.01)
    *G02B 23/24*     (2006.01)
    *G02B 23/26*     (2006.01)
    *G02B 26/10*     (2006.01)
    *A61B 1/00*     (2006.01)
    *A61B 1/06*     (2006.01)
    *G02B 27/40*     (2006.01)
    *G03B 21/14*     (2006.01)

(52) U.S. Cl.
    CPC ........ *A61B 1/00188* (2013.01); *A61B 1/0623* (2013.01); *A61B 1/07* (2013.01); *G02B 23/2469* (2013.01); *G02B 23/26* (2013.01); *G02B 26/103* (2013.01); *G02B 27/40* (2013.01); *G03B 21/142* (2013.01); *H04N 5/23212* (2013.01)

(58) Field of Classification Search
    USPC ........................................................ 250/234
    See application file for complete search history.

(56) References Cited

U.S. PATENT DOCUMENTS

| | | |
|---|---|---|
| 7,233,351 B1 | 6/2007 | Knighton et al. |
| 7,242,833 B2 | 7/2007 | Yang et al. |
| 7,298,938 B2 | 11/2007 | Johnston |
| 7,305,109 B1 | 12/2007 | Gagnon et al. |
| 7,312,879 B2 | 12/2007 | Johnston |
| 7,395,967 B2 | 7/2008 | Melville |
| 7,784,697 B2 | 8/2010 | Johnston et al. |
| 2003/0076571 A1 | 4/2003 | Macaulay et al. |
| 2003/0222197 A1 | 12/2003 | Reese et al. |
| 2004/0076390 A1 | 4/2004 | Dong Yang et al. |
| 2005/0020926 A1 | 1/2005 | Wiklof et al. |
| 2008/0058629 A1 | 3/2008 | Seibel et al. |
| 2008/0249369 A1 | 10/2008 | Seibel et al. |
| 2012/0140301 A1* | 6/2012 | Xu .................. G02B 23/243 359/198.1 |
| 2013/0184524 A1 | 7/2013 | Shimada et al. |

FOREIGN PATENT DOCUMENTS

| | | |
|---|---|---|
| WO | WO 2006/054116 A2 | 5/2006 |
| WO | WO 2010/145669 A1 | 12/2010 |
| WO | WO 2012/132750 A1 | 10/2012 |

OTHER PUBLICATIONS

U.S. Appl. No. 10/956,241, filed Oct. 1, 2004, Johnston.
U.S. Appl. No. 11/094,017, filed Mar. 29, 2005, Johnston et al.
U.S. Appl. No. 12/040,249, filed Feb. 29, 2008, Melville et al.
U.S. Appl. No. 12/468,832, filed May 19, 2009, Melville et al.
International search report and written opinion dated Apr. 29, 2013 for PCT Application No. US2013/026527.
European search report and opinion dated Sep. 21, 2015 for EP Application No. 13748551.

* cited by examiner

EXTENDED DEPTH OF FOCUS FOR HIGH-RESOLUTION OPTICAL IMAGE SCANNING

CROSS-REFERENCE

This application is a U.S. National Phase Application under 35 U.S.C. 371 of International Application No. PCT/US13/26527, filed Feb. 15, 2013, which claims the benefit of U.S. Provisional application No. 61/599,839, filed Feb. 16, 2012, which applications are incorporated herein by reference.

STATEMENT AS TO FEDERALLY SPONSORED RESEARCH

This invention was made with government support under Grant No. R33 CA094303 awarded by the National Institutes of Health. The government has certain rights in the invention.

BACKGROUND OF THE INVENTION

In an image scanning system, a beam of light is typically scanned across a target area and the backscattered or reflected light is modulated in intensity and color to give a pixel at the particular location and time within the scan corresponding to the point on the surface. To increase image resolution or decrease the size of the image pixel, the optical point of interrogation on the surface need to be made sufficiently small. However, when the light is focused to a small spot, the depth of focus or depth of field of the resulting image becomes relatively shallow as well, meaning that only a small portion of the target area remain in focus. There is a need, therefore, to provide an extended depth of focus or field while maintain high image resolution.

SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In many embodiments, improved methods and systems for acquiring and/or projecting images from and/or to a target area are provided. Such methods and systems include an optical fiber assembly which may be driven to scan the target area in a scan pattern. The optical fiber assembly may provide multiple effective light sources that are axially staggered with respect to an optical system that may focus and/or redirect the light from the multiple light sources onto separate focal planes and/or into optical beams having different degrees of collimation. Image data corresponding to the separate focal planes may be combined to generate a composite image with an extended depth of focus or field and an improved image resolution.

In one aspect, a method for acquiring an image of a target area is provided. The method includes scanning an optical fiber assembly in a pattern so as to provide illumination to the target area, the optical fiber assembly comprising a plurality of optical fibers optically coupled to an optical system to focus light from the optical fiber assembly and produce a plurality of focal planes located at different distances with respect to an optical axis in the optical system, collecting, for each of the plurality of focal planes, light reflected from the target area, and generating, based at least in part on the light collected from the target area, a composite image having a depth of field spanning over a distance between the plurality of focal planes.

In one aspect, a system for acquiring images of a target area is provided. The system includes an optical fiber assembly comprising a plurality of optical fibers operable to provide illumination to the target area, an optical system optically coupled with the optical fiber assembly, the optical system operable to focus illumination from optical fiber assembly to produce a plurality of focal planes located at different distances with respect to an optical axis in the optical system, a scanner actuator coupled to the optical fiber assembly configured to actuate distal portions associated with the plurality of optical fibers to scan, either together or individually, in a scan pattern on the plurality of focal planes, and one or more detectors configured to detect, for each of the plurality of focal planes, light reflected from the target area. The system also includes a processor comprising a tangible medium, the tangible medium comprising instructions that when executed cause the processor to generate, based at least in part on the light collected from the target area, a composite image having a depth of field spanning over a distance between the plurality of focal planes.

In one aspect, a method for projecting a composite image to a target area is provided. The method includes scanning an optical fiber assembly in a scan pattern so as to provide illumination to the target area, the optical fiber assembly comprising a plurality of optical fibers optically coupled to an optical system to focus light from the optical fiber assembly and produce a plurality of focal planes located at different distances with respect to an optical axis in the optical system, modulating the intensity of the provided light to create variation in light intensity across the target area, and projecting, based at least in part on the illumination provided to the target area, a composite image onto the target area, the composite image having a depth of field spanning over a distance between the plurality of focal planes.

In one aspect, a system for projecting images onto a target area is provided. The system comprises an optical fiber assembly comprising a plurality of optical fibers operable to provide illumination to the target area, an optical system optically coupled with the optical fiber assembly, the optical system operable to focus illumination from optical fiber assembly to produce a plurality of focal planes located at different distances with respect to an optical axis in the optical system, a scanner actuator coupled to the optical fiber assembly configured to actuate distal portions associated with the plurality of optical fibers to scan, either together or individually, in a scan pattern on the plurality of focal planes, and one or more processors comprising a tangible medium, the tangible medium comprising instructions that when executed cause the one or more processors to project, based at least in part on the illumination provided to the target area, a composite image having a depth of field spanning over a distance between the plurality of focal planes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention provides techniques for creating an extended depth of focus or field while maintaining high image resolution in an image scanning system, such as a scanning fiber endoscope (SFE). Typically, an SFE has a single mode optical fiber that is driven to scan in a scan pattern (e.g., spiral or zigzagged) to deliver illumination in a space-filling area over the surface to be imaged. An optical system (e.g., an objective lens system) between the scanning optical fiber tip and the target area typically defines the image resolution in the SFE and the optical system is typically designed to achieve high spatial resolution while providing shallow depths of focus or field.

According to an embodiment of the present invention, the single scanning optical fiber in an SFE is replaced with an optical-fiber assembly comprising a plurality of optical fibers. The tips of these optical fibers may be axially staggered relative to an optical system that is configured to focus light from the optical fibers onto the target area. The staggered fiber tips may be operable to provide varying light source points which may be focused, by the optical system, into separate or staggered focal points and hence separate focal planes. Each focal plane may be associated with a very limited depth of focus or field of view, but in combination the resulting images of the target area may have a desirable extended depth of focus or field with improved image resolution.

Figure 1:
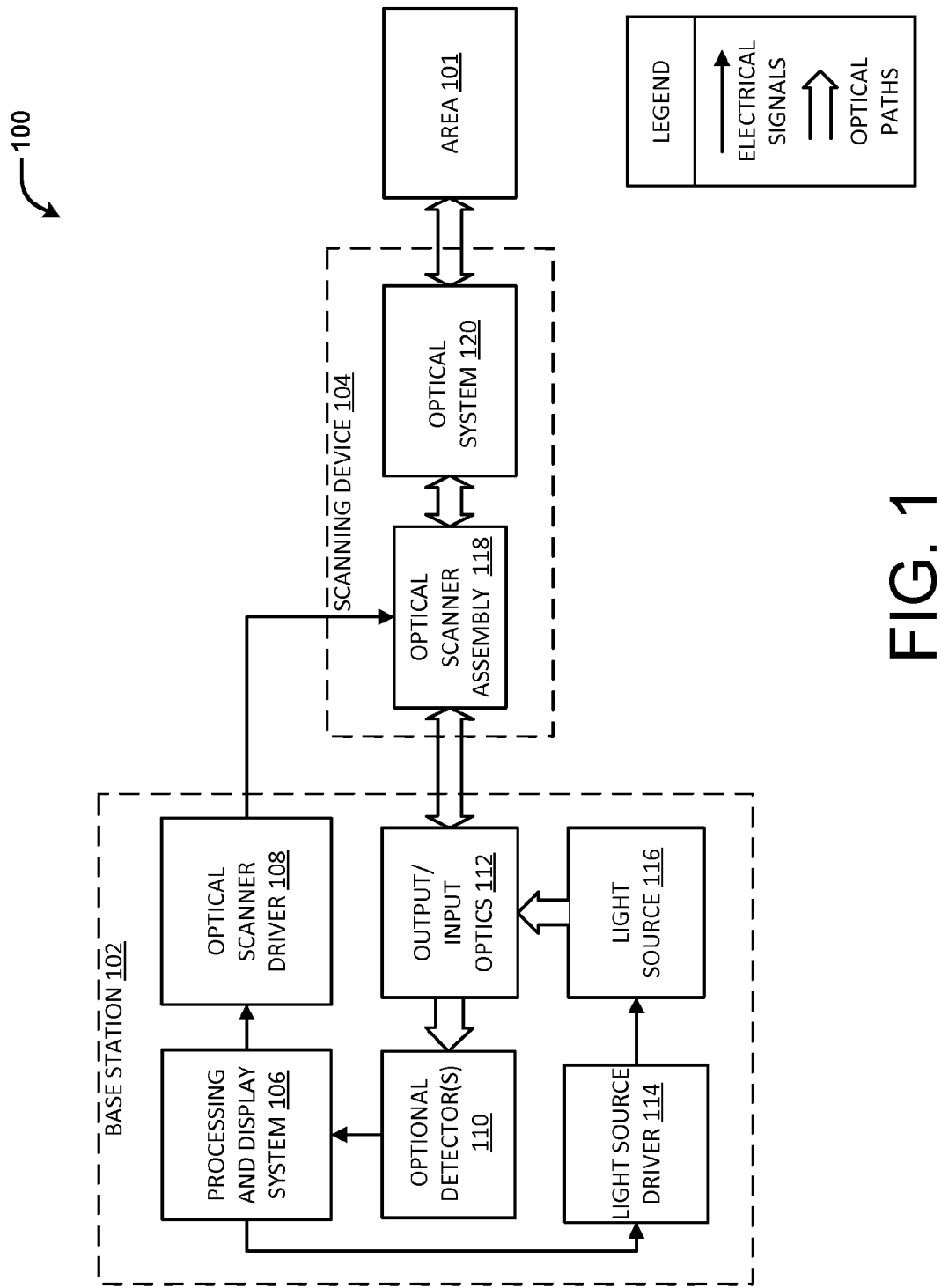
FIG. 1 illustrates components of an example image scanning system for imaging a target area, in accordance with an embodiment.

FIG. 1 illustrates components of an example image scanning system 100 for imaging a target area, in accordance with an embodiment. In some embodiments, the image scanning system 100 may be implemented by an endoscope, bronchoscope, colonoscope or any other type of scopes or instrument to image the surfaces of tissues or organs such as from inside of a body cavity or lumen. More generally, the image scanning system 100 may be used to image any types of surfaces.

In an embodiment, the image scanning system 100 includes a base station 102 and a scanning device 104. The scanning device 104 may be coupled to the base station 102 electronically and/or optically, for example, via one or more cables (not shown). In various embodiments, the image scanning system 100 may include more or less components than those shown in FIG. 1.

The base station 102 may include a processing and display system 106, an optical scanner driver 108, a detector 110, output/input optics 112, a light source driver 114, and a light source 116. In some embodiments, one or more of these elements are omitted. For example, in an embodiment for a fiber scanned display system, the detector 110 is omitted. In another embodiment, the light source driver 114 is omitted.

The processing and display system 106 may include one or more processing units (collectively referred to as the "controller") and a memory (not shown). The memory may comprise a random access memory ("RAM"), a read only memory ("ROM"), and/or a permanent storage device, such as a floppy disc, tape drive, disk drive, DVD/CD-ROM drive, memory card, USB flash drive, solid state drive (SSD) and the like.

In various embodiments, the memory may be coupled to or separate from the controller. The memory may be used for storing software modules, look-up tables, and algorithms that control the operation and any calibration of the image scanning system 100. In some embodiments, a control routine stored in the memory may be used by the processor to control the optical scanner assembly 118 and light source 116. The control routine may be configurable so as to provide operating parameters of the optical scanner assembly 118 (e.g., resonant frequency, voltage limits, zoom capability, color capability, etc.). The memory may also be used for storing data (e.g., images, parameters) received or produced by the processing and display system 106. For example, such data may concern reflection from the target area, imaging data associated with the target area, and the like.

The controller may include one or more microprocessors and/or one or more dedicated electronics circuits, which may include a gate array (not shown). The controller may also include scanner drive electronics, sensor amplifiers and A/D converters (not shown). In various embodiments, the controller may be capable of executing executable instructions or control routines stored in the memory to control various aspects of the image scanning system 100. For example, the controller may be capable of generate, process and/or cause display of images based at least in part on light detected by the detector 110. In an embodiment, the controller also controls actuation of the optical scanner assembly 118 by sending electrical control signals to the optical scanner driver 108. In another embodiment, the controller consists of field programmable gate arrays (FPGA) which are used to condition the fiber scanning pattern and to map the scanned light collection into video image files and display frames. In some embodiments, the controller may also control (e.g., activate) the light source 116 by sending electrical control signals to the light source driver 114. As will be appreciated by those skilled in the art, the methods and techniques of the present invention may be carried out by software modules executed by the controller and/or by electronic hardware.

In some embodiments, the controller is in communication with other elements of the image scanning system 100 via output/input electronics (not shown). The output/input electronics may allow for electrical communication between the controller and the other elements of the image scanning system 100 by providing appropriate interfaces as known in the art.

The processing and display system 106 may optionally include a display (not shown). The display may be used to display images acquired by the image scanning system 100, analysis results and/or other data. For example, the display may be configured to provide real-time images of a patient tissues or organs as they are being scanned, indication of the health or condition of scanned areas and the like. In addition, the display may provide a graphical user interface (GUI) to a user operating the image scanning system. For another example, the display may be used to receive and execute user commands.

In an embodiment, the base station 102 also includes a light source 116 to provide light to the scanning device 104 through one or more output/input optics 112. The light source 116 may include any light source suitable for image acquisition. Examples of suitable light sources include, but are not limited to, lasers, laser diodes, vertical cavity surface-emitting lasers (VCSELs), light-emitting diodes (LEDs), other light emitting devices known in the arts, and combinations thereof. In various example embodiments of the invention, the light source may include a red light source, a blue light source, a green light source, an RGB light source, a white light source, an infrared light source, an ultraviolet light source, a high intensity therapeutic laser light source, or a combination thereof. Depending on the particular implementation, the light source may emit a continuous stream of light, modulated light, or a stream of light pulses. The light sources may be configured to be switchable between a first mode (e.g., continuous stream) and a second mode (e.g., stream of light pulses). If a plurality of light sources are used, a combiner may be used.

In an embodiment, the base station 102 also optionally includes a light source driver 114 configured to communicate electrical control signals to the light source 116 for activating, deactivating or otherwise controlling the one or more light sources. The light source driver 114 may be controlled by a controller of the processing and display system 106 as discussed above.

In an embodiment, the base station 102 also optionally includes an optical scanner driver 108 that communicates electrical drive signals to the optical scanner 18 for actuating cantilevered distal portion of the optical scanner assembly 118, for example, according to an electrical control signal received from a controller of the processing and display system 106 as discussed above. In some embodiments, the drive signals include two drive signals for actuating the optical fiber assembly in a scan pattern about two separate axes. The optical scanner driver 108 may be implemented in hardware (e.g., a circuit), software (e.g., a routine, program, or set of machine-executable instructions), or a combination of both.

In an embodiment, the base station 102 also optionally includes a detector 110, such as a photo detector, for detecting and/or measuring light reflected from the target area. Examples of the detector 110 may include photodiodes, photomultiplier tubes (PMTs) and the like. In many embodiments, the detector 110 converts the reflected light into an electrical signal and communicates the electrical signal to the processing and display system for further processing (e.g., image generation) and/or display.

In some embodiments, the detector 110 may not receive light communicated via the output/input optics 112. Rather, the detector 110 may be placed anywhere where it can detect, and/or optionally measure, light reflected from the target area. For example, in an embodiment, the detector 110 is located inside the optical scanner assembly 118 so as to receive reflected light communicated only through the optical system 120. In another embodiment, the detector 110 is located outside to the optical scanner assembly 118.

In various embodiments, the output/input optics 112 may be used for communicating light from the light source to the optical scanner assembly 118 and/or for communicating reflected light to the detector 110. In various embodiments, the output/input optics 112 may include a waveguide (e.g., optical fiber), a lens assembly or other means for communicating light as is known in the art. In an embodiment, at least a portion of the output/input optics 112 is enclosed in one or more cables connecting the base station 102 and the scanning device 104.

Refer now to the scanning device 104. Typically, the scanning device 104 may be relatively small and maneuverable compared to the base station 102. In some cases, the scanning device 104 may be suitable to be inserted into a body cavity or lumen. In an embodiment, the scanner device 104 includes an optical scanner assembly 118 and optionally an optical system 120. In an embodiment, the optical scanner assembly 118 includes a scanner actuator that is operable to actuate a cantilevered distal portion of a waveguide assembly according to drive signals from the optical scanner driver 108. The drive signals may include two drive signals for actuating the cantilevered distal portion of the waveguide assembly in a scan pattern about two separate axes. In an embodiment, the waveguide assembly includes an optical fiber assembly comprising one or more optical fibers.

In some other embodiments, the optical scanner assembly 118 may include a mirror or other reflective device that may be moved by an actuator to scan a reflected beam. In yet some other embodiments, the optical scanner assembly 118 may include a lens or other focusing device that may be moved by an actuator to scan a focused beam.

The scanning device 104 may optionally include an optical system 120 comprising a lens assembly for directing and focusing light directed out of the optical scanner assembly 118 onto the target area 101. In some embodiments, the optical system 120 may also direct and/or focus light reflected from the target area to the optical scanner assembly 118 and/or to the detector 110.

In some embodiments, the scanning device 104 may include multiple elements or systems such as discussed above (e.g., actuators, waveguides, optical systems scanners and the like) that collectively perform one or more of the functions discussed above.

In some embodiments, the scanning device may implement technologies developed for a scanning fiber endoscope (SFE) as described in numerous commonly owned U.S.

patent applications and patents, which, for example, include: U.S. Pat. No. 7,298,938, entitled "Configuration Memory for a Scanning Beam Device", filed on Oct. 1, 2004; U.S. patent application Ser. No. 10/956,241, entitled "Remapping Methods to Reduce Distortions in Images," filed on Oct. 1, 2004; U.S. Pat. No. 7,159,782, entitled "Methods of Driving a Scanning Beam Device to Achieve High Frame Rates," filed on Dec. 23, 2004; U.S. Pat. No. 7,784,697, entitled "Methods of Driving a Scanning Beam Device to Achieve High Frame Rates," filed on Jan. 3, 2008; U.S. Pat. No. 7,189,961, entitled "Scanning Beam Device with Detector Assembly," filed on Feb. 23, 2005; U.S. patent application Ser. No. 11/094,017, entitled "Methods and Systems for Creating Sequential Color Images," filed on Mar. 29, 2005; U.S. Pat. No. 7,312,879, entitled "Distance Determination in a Scanned Beam Image Capture Device," filed on Aug. 23, 2005; U.S. Pat. No. 7,395,967, entitled "Methods and Systems for Counterbalancing a Scanning Beam Device," filed on Jul. 21, 2005; and U.S. patent application Ser. No. 12/040,249, entitled "Piezoelectric Substrate Fabrication and Related Methods," filed on Feb. 29, 2008; the complete disclosures of which are incorporated herein by reference.

Figure 2:
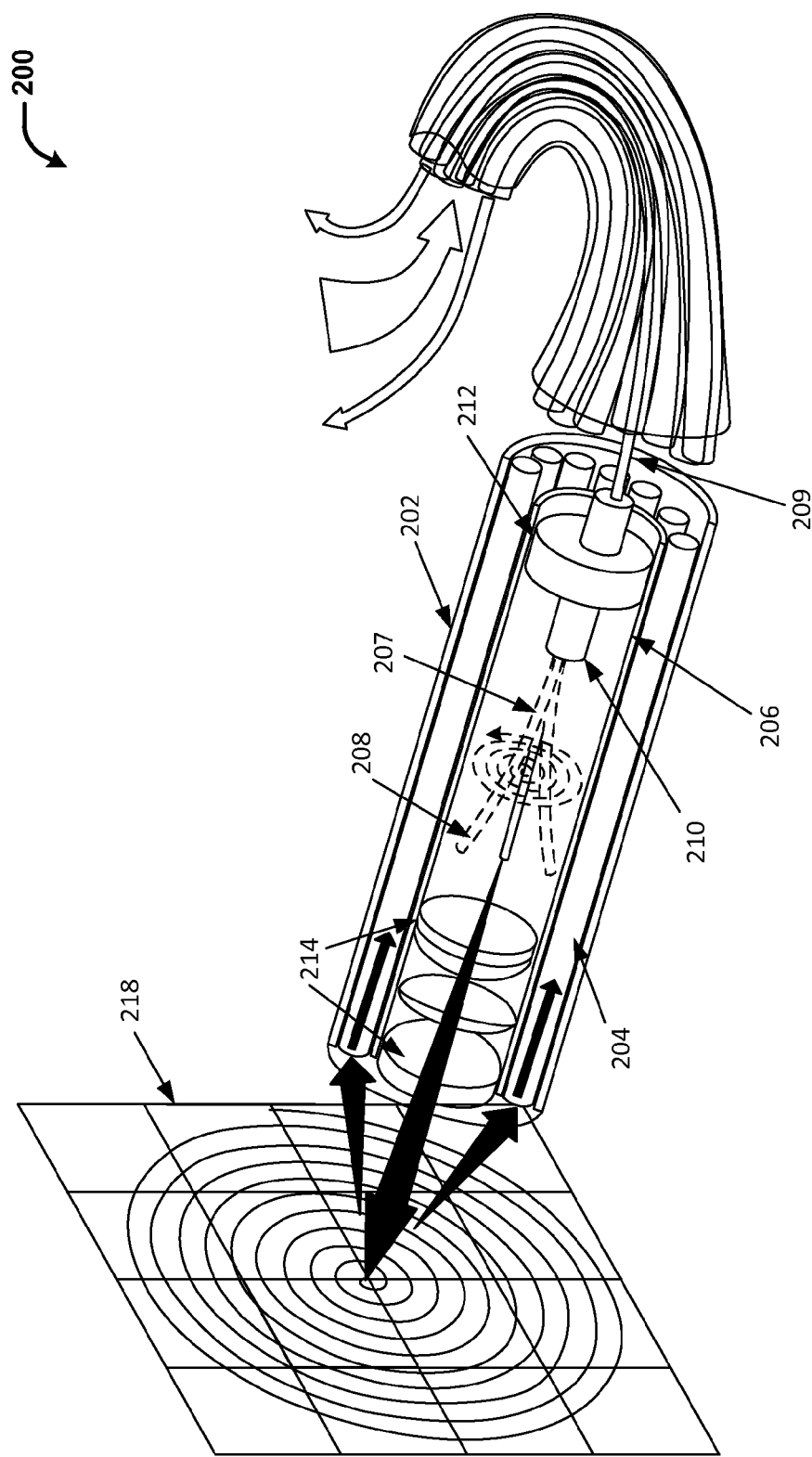
FIG. 2 illustrates an example scanning device that may be used in the image scanning system, in accordance with an embodiment.

FIG. 2 illustrates an example scanning device 200 that may be used in an image scanning system, in accordance with an embodiment. For example, the scanning device 200 may be used in an image scanning system 100 such as discussed in connection with FIG. 1.

In this example, the scanner device 200 includes a cantilevered distal portion 207 of a waveguide assembly 209, with a distal tip 208, mounted within a housing 206. The waveguide assembly 209 may include an optical fiber assembly comprising one or more optical fibers. In other embodiments, the waveguide assembly 209 may include one or more non-optical fiber waveguides. In an embodiment, the waveguide assembly 209 is fixed along at least one point of the waveguide assembly 209 so as to be cantilevered such that the distal portion 207 is free to be deflected. In some embodiments, the cantilevered distal portions of some of the waveguides in the waveguide assembly 209 may be coupled or bound together in a suitable configuration (e.g., side by side) to form a combined cantilevered distal portion. In other embodiments, some or all of the waveguides may not be bound together.

In various embodiments, the cantilevered distal portion 207 of the waveguide assembly 209 may have any desired dimensions and/or cross-sectional profile. For example, the distal portion 207 can have a symmetrical cross-sectional profile or an asymmetrical cross-sectional profile, depending on the desired characteristics of the scanning device. A distal portion 207 with a round cross-sectional profile will typically have substantially the same resonance characteristics about any two orthogonal axes, while a distal portion 207 with an asymmetric cross-sectional profile (e.g., an ellipse) will typically have different resonant frequencies about the major and minor axes. In some embodiments, the distal portion 207 may be linearly or non-linearly tapered along its length.

In an embodiment, the waveguides comprising the waveguide assembly 209 are arranged such that the distal tips of the waveguides are staggered by a small axial distance (e.g., less than 1 to 2 mm) with respective to an optical axis of the optical system 214 (e.g., an objective lens assembly). Thus, when the light coming out of the distal tips of the waveguide assembly 209 is redirected and/or focused by the optical system 214, separate and axially shifted or staggered illumination planes and/or focal planes are created relative to the optical axis of the optical system 214.

In an embodiment, the distal portion 207 of the waveguide assembly 209 is coupled to and actuated by a scanner actuator 210. Examples of suitable types of scanner actuators include, but are not limited to piezoelectric tubes, Electroactive Polymer (EAP) tubes, other actuator tubes, other piezoelectric actuators, other EAP actuators, magnetic actuators, electromagnetic actuators, electrostatic actuators, sonic actuators, electroacoustic actuators, electromechanical actuators, microelectromechanical systems (MEMS), and other transducer capable of moving the cantilevered distal portion of a waveguide assembly.

In an embodiment, an optical scanner driver such as described in connection with FIG. 1 may supply drive signals to the scanner actuator 210 to actuate the distal portion 207 in a scan pattern. The optical scanner driver may be provided inside or outside of the housing 206. The scan pattern may be one dimensional (e.g., zigzag lines) or multi-dimensional (e.g., spiral pattern). In an embodiment, the distal portion 207 of the waveguide assembly 209 is driven at a frequency that is within a Q-factor of the resonant frequency of the distal portion 207, and preferably at its mechanical or vibratory resonant frequency (or harmonics of the resonant frequency). As may be appreciated, the distal portion 207 does not have to be driven at substantially the resonant frequency.

In an embodiment, a housing 206 surrounds the distal portion 207 and the scanner actuator 210. The scanner actuator 210 may be mounted within the housing 206 via one or more collars 212. The housing 206 can also house all or a portion of the optical system 214. The optical system 214 may be spaced from the distal end 208 of the distal portion 207 so as to focus and/or redirect light emitted from the distal end 208 to a target area. In some embodiments, the optical system 214 is provided to facilitate improved image resolution and/or field of view for the optical scanner assembly. In some embodiments, the optical system 214 or one or more components (e.g., lens) thereof may be fixed relative to the distal end 208 of the distal portion 207 and/or relative to the scanner actuator 210. In other embodiments, the optical system 214 or one or more components (e.g., lens) thereof may be movable relative to the housing 206.

In an embodiment, the scanning device 200 comprises an outer sheathing 202 outside the scanner housing 206 that includes one or more return waveguides 204 (e.g., optical fibers). The return waveguides 204 may be configured to carry light reflected from a target area back to a base station for further processing and analysis (e.g., by light detectors, processors and the like). In some embodiments, light detectors may be located so as to receive reflected light via the optical fiber. In some embodiments, the detectors may be located outside the optical path of the waveguide assembly 209. For example, the detectors may be located in a base station or near the distal portion of scanner assembly but outside the housing 206. In other embodiments, the detectors may be located inside the housing 206.

When in use, the waveguide assembly 209 may be driven by scanner actuator 210 to scan, in a scan pattern (e.g., spiral, zigzag), onto one or more illumination planes 218 that are proximal to the distal end of the scanner assembly. Each waveguide of the waveguide assembly 209 may, through the optical system 214, generate an illumination spot on an illumination plane 218. The illumination spot may be located at or near a focal point to enhance image resolution. As such, the illumination plane may coincide with or may be very close to the focal plane associated with the focal point. When the distal ends of the waveguides of the waveguide assembly 209 are axially staggered as described above, separate focal points and hence focal planes associated with the focal points may be created by a single optical system 214. Light reflected from each of these focal planes may be collected and processed to generate an image of extended depth of focus or field deeper than the depth of focus or field associated with any single focal plane.

Figure 3A:
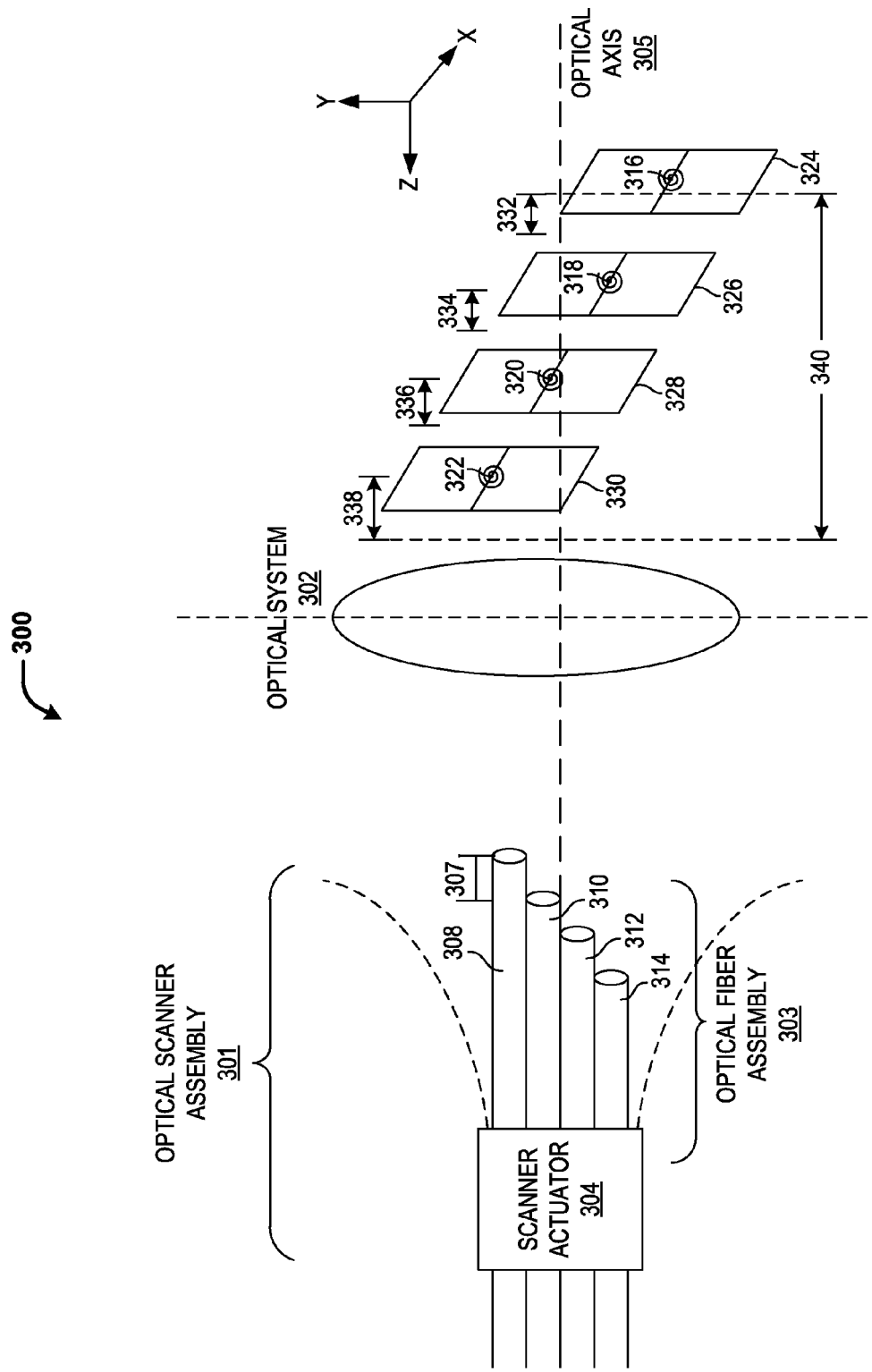
FIGS. 3a-b illustrate example components of a scanning device configured to provide an extended depth of field, in accordance with an embodiment.

FIG. 3*a* illustrates example components of a scanning device 300 configured to provide an extended depth of field, in accordance with an embodiment. The scanning device 300 includes an optical scanner assembly 301 and an optical system 302. The optical scanner assembly 301 includes a scanner actuator 304 and an optical fiber assembly 303. The scanner actuator 304 may be coupled to the optical fibers assembly 303 so as to actuate a cantilevered distal portion of the optical fibers assembly 303 in a scan pattern, as discussed in connection with FIG. 2.

In an embodiment, the optical fiber assembly 303 includes cantilevered portions of a plurality of optical fibers such as 308, 310, 312 and 314. The number, dimensions and material of the optical fibers in the optical fiber assembly 301 may vary in different embodiments, for example, based at least in part on the application of the scanning device. In an embodiment, three or four single mode optical fibers made from silicon dioxide (quartz) material have their claddings etched from the standard 125 microns in outer diameter to approximately 10 to 50 microns diameter in outer diameter and the lengths of the cantilevered portions of the optical fibers are about 2 to 8 mm proximally. Note that in this example, the etching of the claddings is not required; rather, the etching procedure is used simply to save space for microendoscopy application so as to create a multi-waveguide cantilever of approximately the same overall diameter as a 125 micro single optical fiber used in a micro-optical fiber scanner.

In an embodiment, as shown in FIG. 3*a*, the distal portions of the optical fibers in the optical fiber assembly may be arranged in a staggered fashion along an optical axis 305 of the optical system 302 such that distal tips of the optical fibers are of varying distances to the lens of the optical system 302. For example, as shown in FIG. 3*a*, the distal tip of optical fiber 310 may be staggered by a small axial distance 307 (e.g., 1 to 2 mm) from the distal tip of adjacent optical fiber 308. Similarly, the distal ends of optical fibers 312 and 314 may be staggered by a small axial distance from the distal ends of optical fibers 310 and 312, respectively. In various embodiments, the optical fibers may be arranged in various configurations. For example, the staggered distance between adjacent optical fibers need not be uniform. Some of the adjacent optical fibers may not be staggered at all. In some embodiments, the optical fibers may be arranged side by side as shown in FIG. 3*a*. In other embodiments, the optical fibers may be arranged along multiple axes. Some example configurations of the optical fibers are provided in FIG. 7.

In some embodiments, the cantilevered portions of the optical fibers in the optical fiber assembly may be bound or coupled together to form a combined cantilevered portion. The combined cantilevered portion may be etched or tapered to reduce the overall diameter. Various techniques may be used to bind the optical fibers including binding or welding of the optical fibers using carbon dioxide laser, heat, optical epoxy, adhesive chemical, heat-shrunk physical tubing and the like. Such fused cantilevered portion of the optical fibers may be driven by the scanner actuator as a whole in a scan pattern similar to the way a single optical fiber is driven to scan in a scanning fiber endoscope (SFE). In some other embodiments, at least some of the cantilevered portion of the optical fibers in the optical fiber assembly may not be bound together. Instead, some of the cantilevered portions may be free and separate from one another. For example, in an embodiment, the optical fibers may be divided into multiple sub-groups each of which is bound together. In another embodiment, all the optical fibers may be free from each other. In such embodiments, the optical fibers may be actuated, sequentially or simultaneously, by one or more scanner actuators.

In an embodiment, light emitted from the staggered distal tips of the optical fibers 308, 310, 312, and 314 is focused and/or redirected by an optical system 302 to produce corresponding focal points or illumination spots 316, 318, 320 and 322 that are also staggered along the optical axis 305. Typically, the closer the light source is to the lens of the optical system, the further the focal point is along the optical axis from the optical system and vice versa. The focal points 316, 318, 320 and 322 are associated with corresponding focal plane 324, 326, 328 and 330. As used herein, a focal plane is a plane (shown as the plane of X and Y axis in FIG. 3*a*) that passes through a focal point and is perpendicular to an optical axis (shown as the Z axis). As shown, focal planes 324, 326, 328 and 330 are separately spaced along the optical axis each with a corresponding depth of field 332, 334, 336 and 338. Typically, each of these depths of field is intended to be shallow in exchange for a relatively small illumination spot and hence improved image resolution. However, when light reflected from each of the plurality of focal planes collected and processed, a composite image may be generated, based at least in part on imaging data from the multiple focal planes, with a combined depth of the field 340 that spans at least over the distance over the multiple focal planes. Such an extended depth of field 340 may be deeper than the depth of field associated with any of the individual focal planes.

In a preferred embodiment, the optical system 302 remains substantially fixed relative to the optical fiber assembly and/or actuator during the scanning process. Alternatively, the optical system may be moved (e.g., via moving mirrors or lens) to produce a scanning light beam. Advantageously, when the optical system is fixed, the optical fiber assembly may be driven to scan at a scan rate and/or pattern independent of the mechanical limits of the optical system.

It is understood that the focal points and focal planes illustrated in FIG. 3*a* represents all the focal points and focal planes that may occur over time. In some embodiments, the staggered optical fibers may be configured to provide illumination in a sequential manner such that not all focal planes or all portions of the focal planes are illuminated at once. In some embodiments, the sampling of the collected light may be performed at a frame-sequential, line-sequential or even pixel-sequential manner.

Figure 3B:
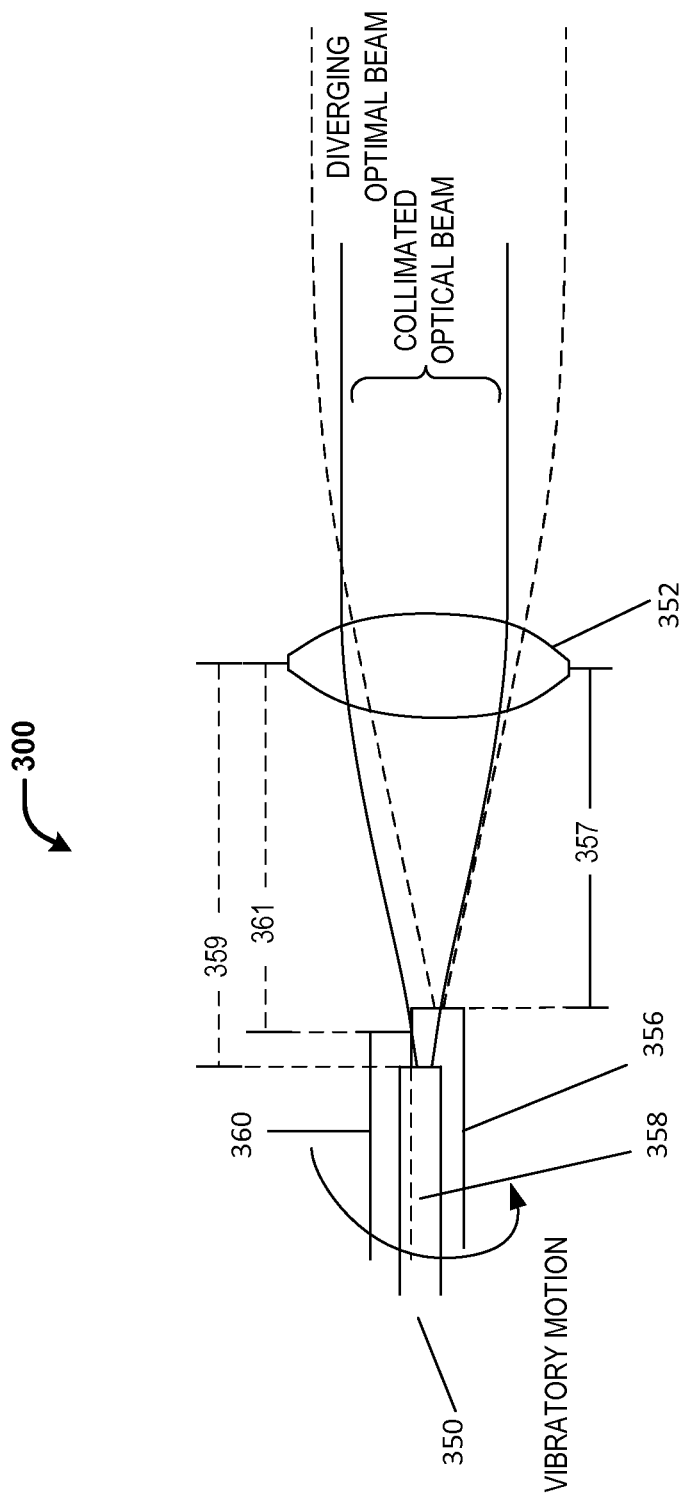

In some embodiments, the optical system may focus and/or redirect light from the optical fiber assembly into light beams with different degrees of collimation. FIG. 3*b* illustrates such an example, in accordance with another embodiment. In this embodiment, the optical fiber assembly 350 includes a plurality of optical fibers 356, 358 and 360 that are arranged such that the distal ends of the optical fibers have staggered ends with different distances 357, 359 and 361, respectively, with respect to an optical system 352. For example, the light emerging from the distal end of the optical fiber waveguide 358 is located at the distance 359 which is equivalent to the focal length of the lens system 352, which results in a more collimated beam of light compared to the other optical fiber tips located closer to the lens system. During the scanning process, the optical fiber assembly 350 may be driven to move in a vibratory motion. As illustrated, due to the different focal length and/or the configuration of the optical system, light beams from the light sources may become mostly collimated (e.g., for optical fiber 358) or divergent (e.g., for optical fiber 356). This embodiment is most relevant to a system that is generating images directly to the eye for a fiber scanning display system that has the capability for displaying images at various depths. The image being scanned with a beam of collimated light, the eye would relax the crystalline lens of the eye to bring the apparent distant image into focus. Whereas, the beams of diverging light would appear out of focus until the eye accommodates to bring the apparent nearer images into focus. In this way a single microdisplay based at least in part on scanning multiple channels of light at different degrees of collimation can generate a true three-dimensional display.

Figure 4:
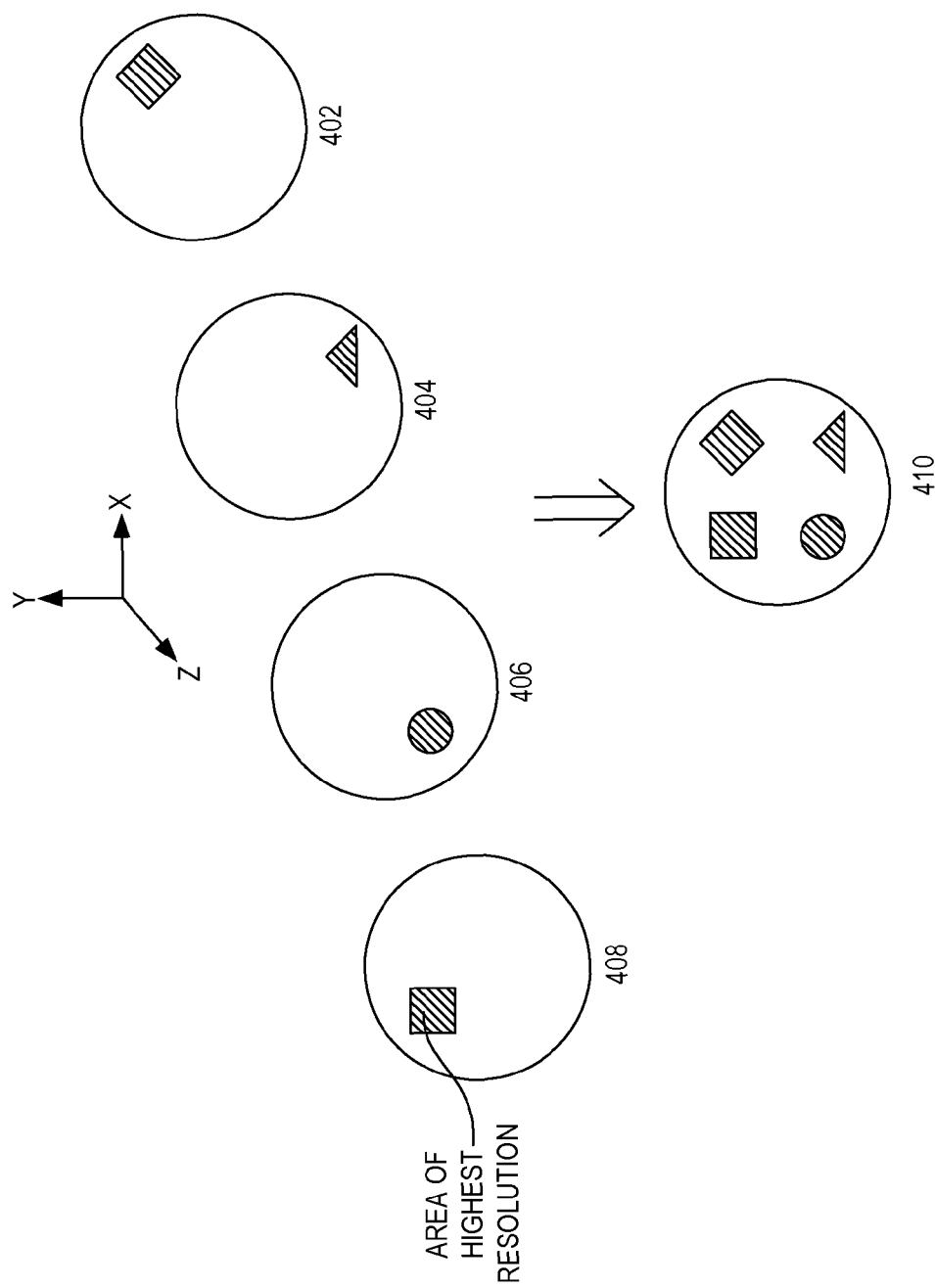
FIG. 4 illustrates example image processing used to provide an image with an extended depth of focus or depth of field and improved resolution, in accordance with an embodiment.

As discussed above, each focal or illumination plane associated with each of the plurality of optical fibers may have a very limited depth of focus or field of view. However, in combination, the resulting images of the target area may have the desired extended depth of field at a high resolution. FIG. 4 illustrates example image processing to provide an extended depth of field, in accordance with an embodiment. In this example, light reflected from each of the plurality of illumination or focal planes generated by staggered-tipped optical fiber assembly may be collected (simultaneously or separately) and processed to generate a plurality of image data sets for a target area. Each image set of the plurality of image data sets may correspond to an image for one of the plurality of focal planes. For example images data sets 402, 404, 406 and 408 may be generated for focal planes 332, 334, 336 and 338, respectively, discussed in connection with FIG. 3a. Since each focal plane is associated with a limited depth of focus or depth of field, only a small portion of corresponding image (indicated by shaded areas in FIG. 4) may have a high resolution relative to the rest of the image. In an embodiment, each image data set may be processed or analyzed, for example, by an image processing system 106 discussed in connection with FIG. 1, to identify the regions or pixels within the image with the highest focus or resolution. In an embodiment, such identified high-resolution regions or pixels across multiple images may be combined into a composite image 410 of the target area. Thus, the composite image 410 has an effective depth of field that extends beyond the depths of field associated with the individual focal planes.

Figure 5:
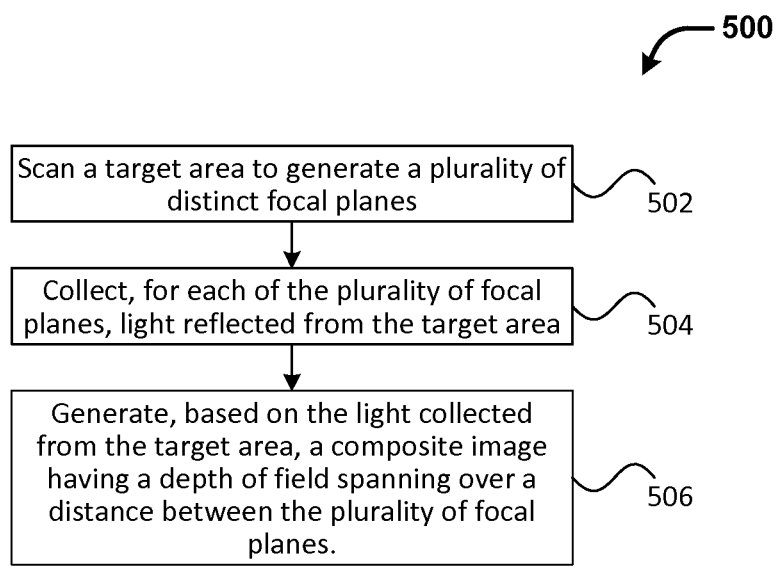
FIG. 5 illustrates an example process for acquiring an image of a target area, in accordance with an embodiment.

FIG. 5 illustrates an example process 500 for acquiring an image of a target area, in accordance with embodiments. Aspects of the process 500 may be performed, for example, by the image scanning system 100 discussed in connection with FIG. 1. Some or all of the process 500 (or any other processes described herein, or variations and/or combinations thereof) may be performed under the control of one or more computer/control systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. The order in which the operations are described is not intended to be construed as a limitation, and any number of the described operations may be combined in any order and/or in parallel to implement the processes.

In an embodiment, process 500 includes scanning 502 the target area to generate a plurality of distinct focal planes. In an embodiment, an optical fiber assembly comprising a plurality of optical fibers may be actuated to scan in a scan pattern on the target area through an optical system, such as discussed in connection with FIG. 3a. The distal tips of the plurality the optical fibers may be axially staggered relative to an optical axis of the optical system such that the resulting focal points and hence focal planes are also axially staggered or spaced apart. In various embodiments, the staggered optical fibers may be configured to illuminate the respective scanning planes, sequentially or simultaneously, individually or as a whole.

Light reflected from the target area may be collected 504, for example, by one or more lens and/or light-collection optical fibers and provided to one or more detectors such as discussed in connection with FIG. 1. For example, the light may be emitted and detected from the same optical fiber in a confocal arrangement. In various embodiments, light collection and/or detection may be performed in a frame-sequential, scan-line-sequential pixel-sequential or any suitable manner. In an embodiment, the collection fibers and/or detectors may be divided into two or more groups based at least in part on the relative position and/or orientation of the fibers tips. For example, the fibers may be divided into four quadrants based at least in part on their positions relative to the scanning fiber tips. In an embodiment, the collection fibers and/or detectors may be divided into two or more groups according to the optical fibers in the optical fiber assembly.

In an embodiment, each of the plurality of illumination or focal planes is scanned in sequence and the backscattered light associated with each of the illumination or focal planes is collected and detected in sequence. In another example, two or more of the plurality of illumination or focal planes are scanned at a time and the backscattered light associated with the two or more illumination or focal planes is collected and detected at a time. When the planes are scanned in sequence, the same set of detectors may be used to detect light associated with different illumination planes. In yet another embodiment, all of the illumination or focal planes are scanned simultaneously and the backscattered light associated all of the planes is collected at once.

Based at least in part on the detected backscattered light reflected from the target area, a composite image having a depth of field spanning over a distance between the plurality of focal planes may be generated 506. To generate the composite image, image data associated with each of the focal planes may be processed and/or combined. For example, for a given pixel or a set of pixels in a particular region of the composite image, the image data associated with various focal planes may be analyzed to extract the image data with the highest resolution. In other words, knowing beforehand where the focal depth is for each of the plurality of optical fibers, the regions or pixels of highest focus may be combined in a three-dimensional mapping to the correct X and Y pixel location of the image and the Z location of each of the plurality of focal planes. In other embodiments, other suitable image processing techniques may also be used to otherwise combine the image data. For example, for a given pixel or set of pixels, image data along the Z axis may be averaged to calculate the data for the composite image at that pixel or set of pixels.

In some embodiments, the composite image may be a two-dimensional image or a three-dimensional image illustrating the depths associated with the target area. In some embodiments, two or more composite images may be generated, each derived at least in part from all or a subset the image data associated with the plurality of focal planes.

Figure 6:
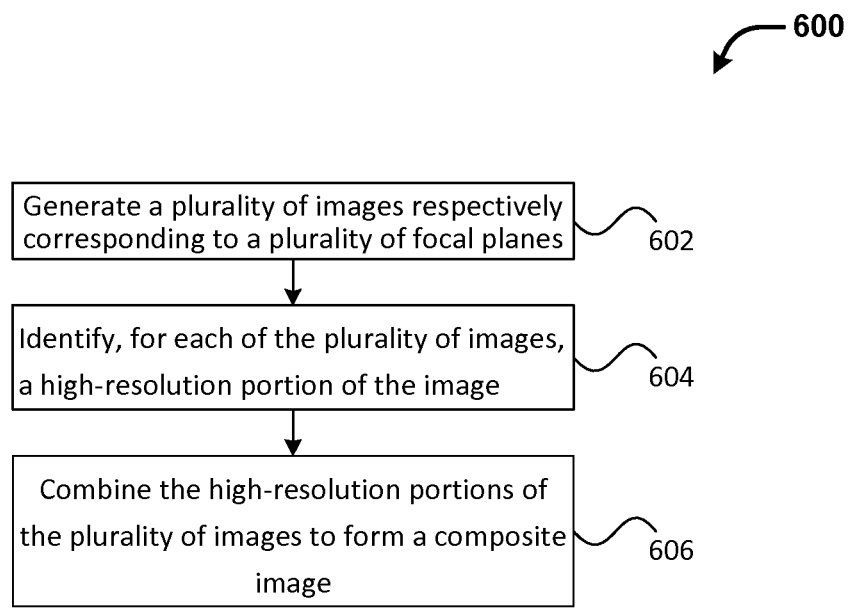
FIG. 6 illustrates an example process for generating a composite image of a target area with an extended depth of focus or depth of field, in accordance with an embodiment.

FIG. 6 illustrates an example process 600 for generating a composite image of a target area with an extended depth of field, in accordance with embodiments. Process 600 may be implemented as part of step 506 of process 500 discussed above in connection with FIG. 5. Aspects of the process 600 may be performed, for example, by the image processing and display system 106 discussed in connection with FIG. 1.

In an embodiment, process 600 includes generating 602 a plurality of images respectively corresponding to the plurality of focal planes. In some embodiments, generating 602 the plurality of images includes scanning a target area on a plurality of focal planes, simultaneously or sequentially, individually or as a whole, collecting and detecting the backscattered light as a result of the scan, and generating images corresponding to each of the plurality of focal planes. In other embodiments, rather than generating a separate image for each of the focal planes, a collection of image data representing some or all of the focal planes may be generated and analyzed.

In an embodiment, process 600 includes identifying 604, for each of the plurality of images, a high-resolution portion of the image. For example, image data associated with each pixel or a collection of pixels may be analyzed. In some embodiments, given the relative positions and orientation of the scanning optical fiber tips, certain characteristics associated with each of the focal planes, such as the location of the highest-resolution portion of the image, may be pre-calculated.

In an embodiment, process 600 includes combining 606 the high-resolution portions of the plurality of images to form the composite image. Various image processing techniques, such as image stitching techniques, may be used. In some embodiments, rather than selecting only the highest-resolution portions, the image data associated with images of various depths of focus or field may be combined in other ways (e.g., averaged).

In various embodiments, methods, systems and/or components described herein may be used for image acquisition, image display/projection or both. For example, the techniques described herein may be used in a scanning laser display system such as described in U.S. patent application Ser. No. 12/468,832, entitled "Scanning laser projection display devices and methods for projecting one or more images onto a surface with a light-scanning optical fiber," filed on May 19, 2009, the disclosure of which is incorporated herein by reference. In other words, the image acquisition techniques using staggered fiber tips described herein can be used in reverse, as image display techniques. In such a display system, the light scanned across a target area is modulated over time, such that image elements are rendered in the target area. By providing different image data via different fibers or other light sources that are scanned across space, multiple display focal planes can be generated. When viewed by the eye, these multiple focal planes may be viewed as a volumetric or stereo 3D image.

To this end, a 3-D scene or object may be sliced, by one or more processors, into a plurality of discrete focal planes or layers. Each of the focal planes may be associated with a limited depth of focus or depth of field but in combination, the focal planes may cover a full range of focus for the 3-D scene or object. In an embodiment, an optical fiber assembly such as disclosed herein may be articulated in a scan pattern as discussed herein. When articulated, each optical fiber in the optical fiber assembly may be configured to display an image representation associated with one of plurality of focal planes discussed above. In various embodiments, image representations associated with the plurality of discrete focal planes may be displayed simultaneously or sequentially onto a target surface such as an eye.

Referring now to FIG. 1, the image scanning system 100 may be configured to provide functionalities related to image acquisition, image projection, or both. For example, in an embodiment, the image scanning system 100 may be used as a projection system for projecting or displaying one or more images onto an area. The projection system may be used in a wide range of applications, for example, mobile phones, laptops, personal digital assistants (PDAs), MP3 players, smart phones, digital cameras, camcorders, personal mobile televisions, portable projection units, GPS enabled devices, and automobiles.

In an embodiment, the processing and display system 106 includes a memory for storing a 3-D model of an object or a scene to be projected onto an area. The 3-D model may be computer-generated. The processing and display system 106 may also include one or more processors configured to generate a plurality of image representations based on the 3-D model. For example, 3-D model may be "sliced" into a plurality of 2-D images corresponding to distinct focal planes (e.g., along an optical or Z axis). In various embodiments, each focal plane may be associated with one or more image representations or sets of image data. Such images or image data may be stored in the memory. Based at least in part on the image data, the processing and display system 106 may generate control signals to the optical scanner driver 108 to control the scanner actuator in the optical scanner assembly 118 as well as control signals to the light source driver 114. In an embodiment, each optical fiber is controlled by a separate light source driver. In such an embodiment, the signals received by a light source driver may be generated in response to image data for one of the focal planes. In another embodiment, two or more optical fibers may share the same light source driver.

In an embodiment, the detectors 110 may be omitted from the projection system. In another embodiment, the detectors 110 may be used to detect and/or measure light reflected from the projection area 101 to generate feedback signals concerning the projected images. The feedback signals may be processed by the processing and display system 106. For example, by correlating where the projected light is in the scan pattern with the reflected light detected/measured, information relating to the image and any interactions with the image can be determined.

Referring now to FIG. 3, the scanning device 300 may be used for image projection purposes instead of or in addition to image acquisition purposes, in accordance with an embodiment. In this example, the optical fiber assembly 301 is coupled to the scanner actuator 304, which actuates the cantilevered distal portion of the optical fiber assembly to scan in a scan pattern. Light scanned across a target area is modulated over time, such that image elements are rendered in the target area. By providing different image data via different fibers or other light sources (such as provided by a multi-channeled cantilever assembly discussed in connection with FIG. 10) that are scanned across space, multiple display focal planes such as 324, 326, 328 and 340 can be generated. When viewed by the eye, these multiple focal planes may be viewed as a volumetric or stereo 3D image.

Figure 11:
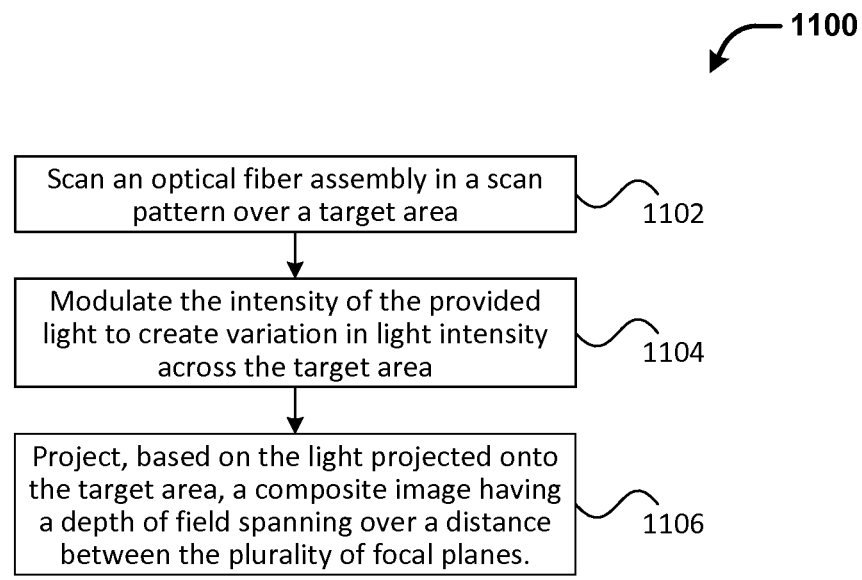
FIG. 11 illustrates an example process for projecting a composite image onto an area, in accordance with embodiments.

FIG. 11 illustrates an example process 1100 for projecting a composite image onto an area, in accordance with embodiments. Aspects of the process 1100 may be performed, for example, by the image scanning system 100 discussed in connection with FIG. 1. In an embodiment, the composite image may include a 3-D or stereo image comprising one or more 2-D images.

In an embodiment, process 1100 includes scanning 1102 an optical fiber assembly such as discussed herein in a scan pattern so as to provide illumination to an area, the optical fiber assembly comprising a plurality of optical fibers optically coupled to an optical system to focus light from the optical fiber assembly and produce a plurality of focal planes located at different distances with respect to an optical axis in the optical system. In an embodiment, a 3-D composite image or 3-D model of a scene or object may be generated or obtained. The 3-D composite image or model may be processed to determine a plurality of 2-D images associated with different focal planes. Control signals may be determined from the optical scanner driver and/or light source driver(s) discussed above. Such control signals may be used to articulate the optical fiber assembly so as to generate the plurality of 2-D images for the 3-D composite image or model. In some embodiments, the composite image may be generated based at least in part on the light provided to the target area. In various embodiments, the optical fiber assembly may be configured to project the plurality of 2-D images in simultaneously or sequentially.

In an embodiment, process 1100 includes modulating 1104 the intensity of the provided light to create variation in light intensity across the target area. In many embodiments, light source intensity, image size, scanning pattern, and/or scanning parameters are varied and/or modified to achieve desired image characteristics. Such variations and/or modifications can be used to achieve desired image characteristics for a variety of target surface characteristics (e.g., size, orientation, and reflectivity) and ambient conditions (e.g., illumination). In an embodiment, the modulation of the light intensities is based at least in part on the image or images to be projected.

In an embodiment, process 1100 includes projecting 1106, based at least in part on the light provided to the target area, a composite image having a depth of field spanning over a distance between the plurality of focal planes. As discussed above, in an embodiment, the composite image is generated based at least in part on a 3-D model or image contained within a processing and display system such as discussed in connection with FIG. 1. In an embodiment, the composite image may be generated by superimposing the plurality of 2-D images projected by the plurality of optical fibers in the optical fiber assembly. Each of the focal planes may be associated with a limited depth of focus or depth of field but in combination, the focal planes may cover a full range of focus for the 3-D scene or object.

In an embodiment, detectors may be used to detect and/or measure light reflected from the projection area to generate feedback signals concerning the projected images. The feedback signals may be processed by the processing and display system 100. For example, by correlating where the projected light is in the scan pattern with the reflected light detected/measured, information relating to the image and any interactions with the image can be determined.

Figure 7:
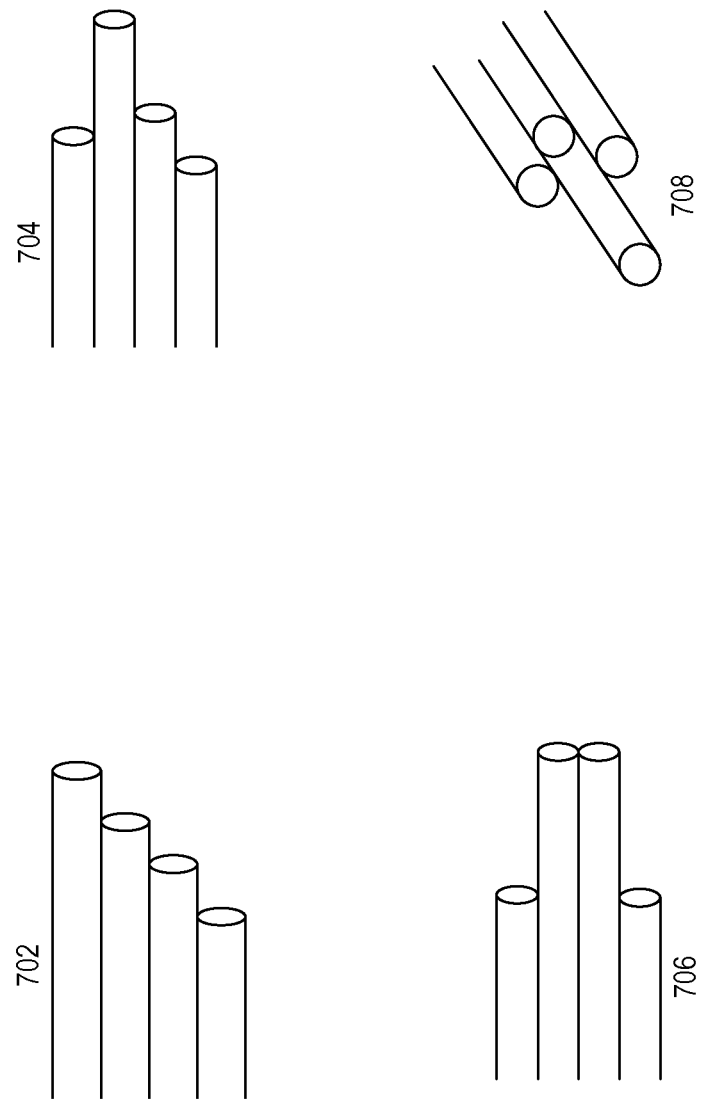
FIG. 7 illustrates some example configurations of optical fibers in an optical fiber assembly, in accordance with some embodiments.

FIG. 7 illustrates some example configurations of optical fibers in an optical fiber assembly, in accordance with some embodiments. In various embodiments, the number, dimension, relative positions and other characteristics of the optical fibers may be configured as desired based at least in part on various considerations such as the application of the optical fiber assembly and/or scanning device. In some embodiments, the optical fibers may be arranged side by side as in configurations 702, 704 and 706 such that the axes of all the optical fibers are in one plane. In other embodiments, the optical fibers may be arranged such as shown in configuration 708 such that at least some of the axes are in different planes.

In an embodiment, such as shown in configuration 702, the tips of adjacent optical fibers are staggered along one direction (e.g., toward the proximal or distal direction) from an outermost optical fiber toward the other outermost optical fiber. In another embodiment, such as shown in configuration 704, the tips of adjacent optical fibers are staggered in more than one direction (e.g., toward the proximal and the distal directions) from one outermost optical fiber toward the other outermost optical fiber. In yet another embodiment, such as shown in configuration 706, at least two of the optical fibers are flush (i.e., not staggered) at the tips.

While four optical fibers are shown here to illustrate certain concepts, it is understood that in various embodiments, the optical fiber assembly may include more or less than four optical fibers. In addition, the optical fibers may have the same or different cross-section profiles, materials and the like. For example, one of the optical fibers may have a thicker core and/or cladding than another optical fiber. For another example, one of the optical fibers may be a multi-mode optical fiber while the others may be single-mode optical fibers. In some embodiments, the claddings of at least some of the optical fibers may be etched or otherwise tapered at the distal portions to decrease the overall diameter of the optical fibers. The numerical aperture of the light emitting from the optical fiber or waveguide may be different due to the inherent structure of the waveguide (e.g. refractive indices) or due to microlens on the distal end of the waveguide.

In various embodiments, the end faces or tips of the optical fibers in the optical fiber assembly may be fabricated with a geometry and/or design to reduce light loss or back reflection. For example, in an embodiment, the axially staggered tips of the optical fibers is encased in a refractive index matching medium so there is little or no air-glass surfaces that would scatter light before light emerges from a single end face. The material for the refractive index matching medium may include an index-matching optical epoxy. In an embodiment, each optical fiber is fused to a strand of glass rod (not an optical fiber with core and cladding materials), then etched, and the optical fiber material is staggered while the glass rod material is cut at the same point for all waveguides to be fused together.

Figure 8:
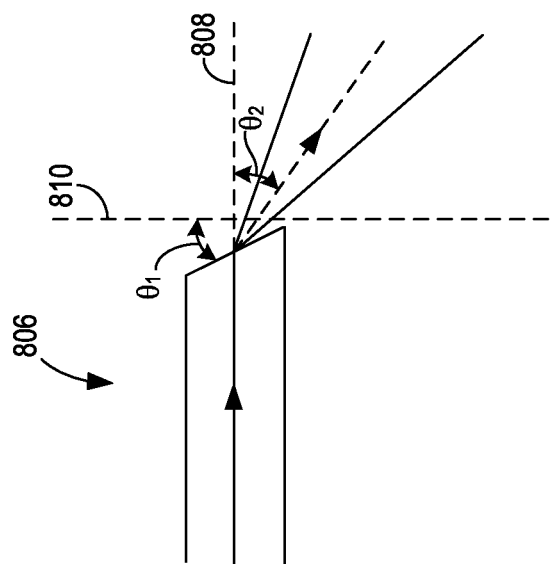
FIG. 8 illustrates some example optical fibers with angled end faces in an optical fiber assembly, in accordance with some embodiments.
Figure 8:
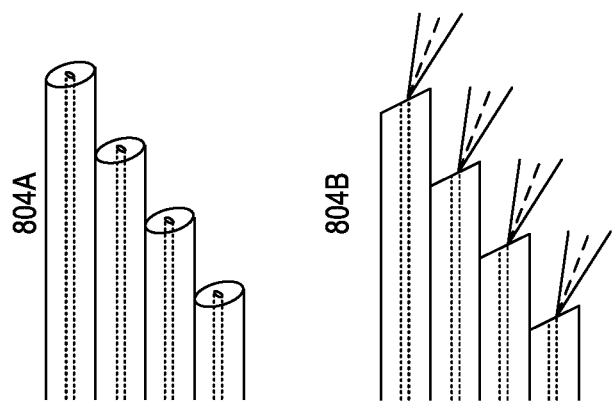
Figure 8:
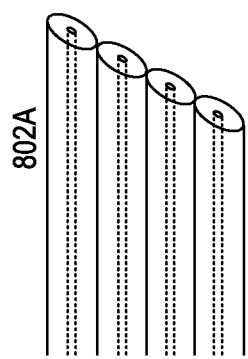
Figure 8:
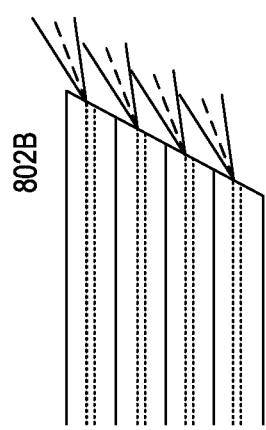

In some embodiments, individual end faces of staggered optical fibers may be cut at a small angle so that the emerging cone of light from the optical fibers do not strike adjacent optical fiber that may extend beyond the shorter optical fiber. FIG. 8 illustrates some examples optical fibers in an optical fiber assembly with angled end faces, in accordance with some embodiments. For example, as shown, the end faces of optical fibers in optical fiber assembly 802A are cut at an angle relative to an axis perpendicular to the axis of the optical fiber cores, such that the resulting end faces form a smooth slanted optical surface. In various embodiments, the exact angle to be cut may depend on the staggered distance between optical fibers, refraction index of the end face materials, characteristics of the optical system used to focus the light, location of the target area and other considerations. A cross-section view of the optical fiber assembly 802A is provided as 802B. As shown, light comes out of such an angled end face at an angle relative to the axis of the fiber, for example, due to the refractive index of the end face material.

Advantageously, cutting the end faces of the optical fibers according to configuration 802A and B may facilitate simplified manufacturing of staggered optical fiber tips discussed herein. Specifically, rather than cutting (at an angle or not) and polishing the end face of each optical fibers individually and binding them in a staggered fashion, the optical fibers may be simply bound together in a bundle without regard to whether the fiber tips are aligned or staggered. Thereafter, the distal portion of the combined optical fiber bundle may be cut and polished as a whole, rather than individually, to produce a smooth slanted optical surface.

A different end face configuration for the optical fibers in an optical fiber assembly is shown by 804A and B (cross-section view). As shown, the end faces of the optical fibers are cut at an angle relative to the axis perpendicular to the axis of the optical fiber cores. However, the angled end faces are shown as facing an opposite direction as that shown in configuration 802A and B.

A close-up view of an angled end face of an optical fiber 806 is provided. As shown, the end face of the optical fiber may be cut at an angle $\theta_1$ relative to an axis 810 perpendicular to the axis 808 of the optical fiber core. The resulting light or light cone coming out of the optical fiber tip may deviate from the axis 808 of the optical fiber core at an angle $\theta_2$. In various embodiments, the end face angle $\theta_1$ and/or the end face material may be adjusted to vary the resulting light cone angle $\theta_2$.

Figure 9A:
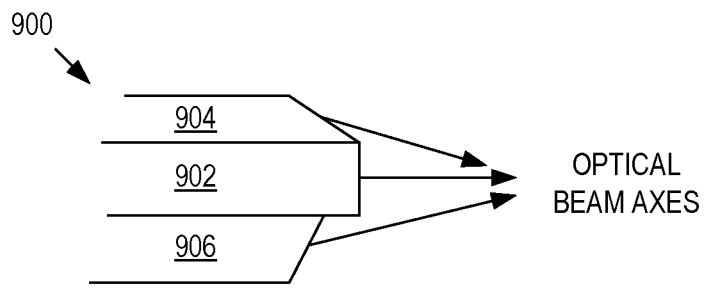
FIGS. 9a-c illustrate an example optical fiber assembly, in accordance with an embodiment.
Figure 9B:
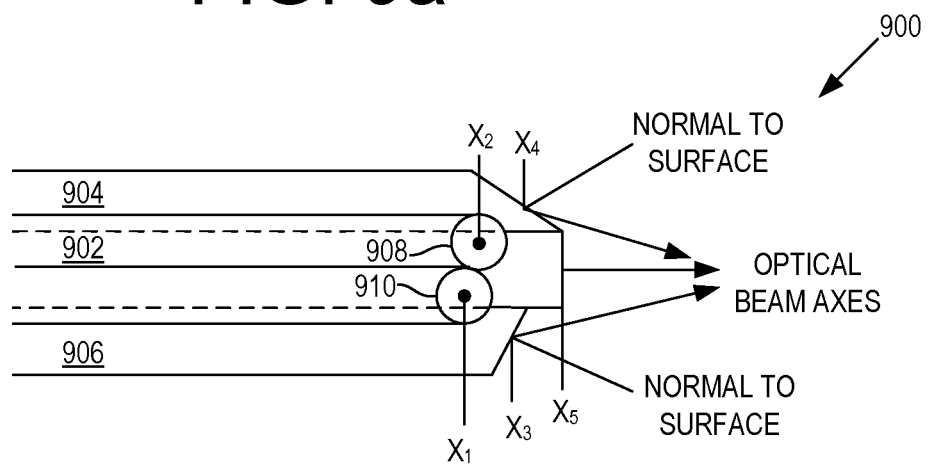
Figure 9C:
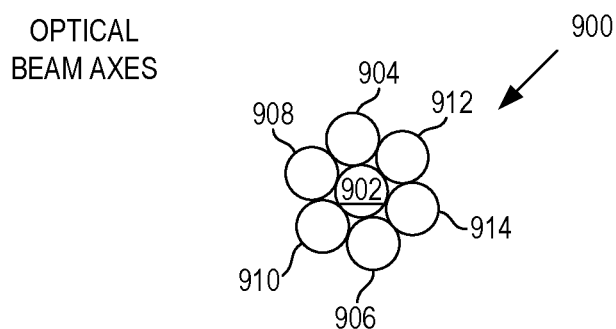

FIGS. 9a-c illustrate an example optical fiber assembly 900, in accordance with an embodiment. In this example, the optical fiber assembly 900 includes a bundle (e.g., seven) of optical fibers with axially staggered distal ends, where one optical fiber is in the center of the bundle surrounded by the rest of the optical fibers. In some embodiments, the center optical fiber may or may not have the longest distal length such that the distal end of the center optical is the closest to the optical system. In some embodiments, at least some of the optical fibers may have the same distal length so that their distal tips are flush at the end face. While FIGS. 9a-c show seven optical fibers in the optical fiber assembly, it is understood that in various embodiment more or less optical fibers than shown may be included in the optical fiber assembly.

FIG. 9a illustrates a cross-sectional view showing three of the seven optical fibers of the optical fiber assembly 900. As shown, the center fiber 902 has an un-angled end face that is perpendicular to the core axis of the optical fiber whereas the surrounding fibers 904 and 906 may have angled end faces facing away from the center optical fiber. In this way, the light beams emerging from the distal ends of the optical fibers may overlap off the distal end for the application to form a distal plane where all optical beams intersect distally from the tip along an axis of the optical fiber assembly 900. The end faces of the optical fibers 904 and 906 may be cut at the same or different angles. In various embodiments, the characteristics of the emerging optical beams may vary due to the different (e.g., staggered) lengths of the distal portions of the optical fibers. In some embodiments, different numerical apertures may be applied to the optical fibers to compensate for such different characteristics resulting from the staggered distal lengths.

FIG. 9b illustrates a side view showing five of the seven optical fibers of the optical fiber assembly 900. As shown, the distal ends of the cores of the optical fibers 902, 904, 906, 908 and 910 may be located at different locations (e.g., x5, x4, x3, x2 and x1, respectively) along a longitudinal axis 920 of the optical fiber assembly 900.

FIG. 9c illustrates an end view showing the seven end faces of the optical fiber assembly 900. As shown, the optical fiber assembly 900 comprises the center optical fiber 902 surrounded by six optical fibers 904, 906, 908, 910, 912 and 914.

In some embodiments, the angle of the tip of the optical fiber can be different for at least some of the optical fibers in an optical fiber assembly. For example a sharper angle could be used for the longer fiber or fiber core further from the bundle central axis, while a shallower angle can be used for a shorter fiber or fiber core closer to the fiber bundle optical axis. The purpose may be to bring at least some of the angled beams together at the same optical beam size at the same plane distal to the optical fiber assembly.

In some embodiments, the overall diameter of an optical fiber could be different for at least some of the optical fibers such that the cores of the optical fibers would be located at different lateral distances from the central axis of the optical fiber assembly.

In some embodiments, the numerical aperture for at least some of the optical fibers could be different. The numeric apertures may determine the size of the optical beam (cross-sectional diameter) over length from the tip of the optical fiber. Such different numeric apertures may be provided by micro-lenses or other optical components located at the tips of the optical fibers.

In some embodiments, instead of an optical fiber assembly, a multi-channeled cantilever assembly with staggered tips may be used. The material of this mechanical cantilever can be fabricated from one or more of a non-optically transmissive property, such as metal, ceramic, or plastic with the capacity (e.g. embedded wires) to bring electrical energy to the distal tip where light is being generated, and optionally to dissipate heat. The multi-channel cantilever may be driven (e.g., by a piezoelectric actuator) to scan in a scan pattern similar to the way an optical fiber assembly is driven to scan. In an embodiment, the multi-channel cantilever may be driven at or near its mechanical resonance for amplification of its lateral vibratory scan motion. FIGS. 10a-d illustrate some example mechanical cantilever assemblies, in accordance with some embodiments. FIG. 10a illustrates an end view of an example multi-channeled cantilever assembly 1000. As shown, the multi-channeled cantilever assembly 1000 may include three light-delivering members 1002, 1004 and 1005, each configured to provide illumination from respective distal light sources 1003, 1005 and 1007 such as Light Emitting Diode (LED) or vertical cavity surface emitting laser (VSCEL).

Figure 10B:
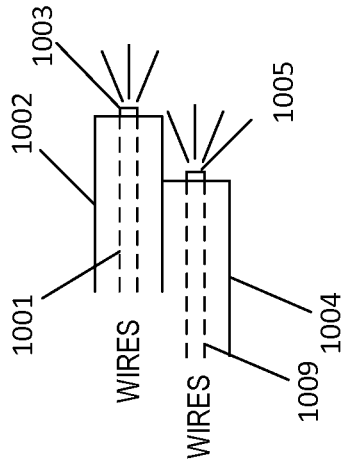
FIGS. 10a-d illustrate some example mechanical cantilever assemblies, in accordance with some embodiments.

FIG. 10b illustrates a cross-sectional view of the multi-channeled cantilever assembly 1000, in accordance with an embodiment. The view shows two of the three light-delivering members 1002 and 1004. In this embodiment, each light-delivering member includes a light source at a distal end of the light-delivering member. For example, the light-delivering members 1002 and 1004 include distal light sources 1003 and 1005, respectively. Power or electrical signals to the light sources may be provided externally by wires (e.g., wires 1001 and 1009) and/or by batteries coupled to the light sources. In some embodiments, the wires may be enclosed within the light-delivering members. In some embodiments, such as shown in FIG. 10b, the light delivering members may be arranged in an axially staggered manner such that the distal light sources are staggered along a longitude axis of the mechanical cantilever.

Figure 10D:
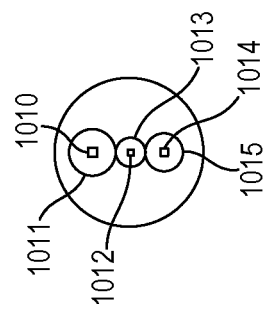
Figure 10A:
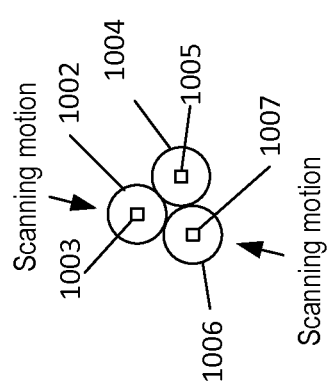
Figure 10C:
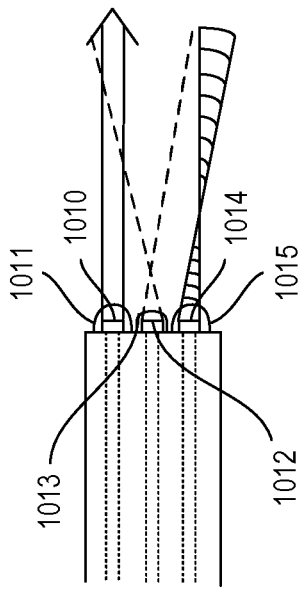

In other embodiments, such as shown in a cross-sectional view in FIG. 10c, the distal light sources may not be axially staggered along a longitude axis as shown in FIG. 10b.

Rather, other mechanisms may be used to vary the characteristics associated with the light sources. For example, some of the light sources such as light sources 1010, 1012 and 1014 may have one or more micro-lens or other optical components optically coupled to the light sources (individually or as a group) such that the emerging light beams may be of different size, collimation, intensity and/or other characteristics. Some of the light sources may not be coupled to any micro-lens or optical components at all.

FIG. 10*d* illustrates an end view of the mechanical cantilever shown in FIG. 10*c*. As shown, the light sources 1010, 1012 and 1014 may be coupled, respectively to micro-lenses 1011, 1013 and 1015. The micro-lenses may be of different characteristics including powers. For example, the micro-lens 1011, 1015 and 1013 may be of increasing power. In various embodiments, the use of micro-lens and/or the types of micro-lens to use may depend on the application of the mechanical cantilever.

In various embodiments, any light source may be used as distal light sources including LED, VSCEL and the like. For example, the distal light sources in FIG. 10*b* may be LED sources whereas the distal light sources in FIG. 10*c* may be VSCEL sources. In some embodiments, a single mechanical cantilever may include light sources of the same or different types.

The example embodiments described above is only representative of many different ways of projecting or acquiring multi-focal images simultaneously or sequentially. In additional embodiments, multiple scanning fiber and optical systems may be employed in parallel to acquire or project multiple images at high resolution and short focal depth, while in combination these images create a single image or multiple composite or stereo images of high resolution and extended depth(s) of focus or field.

An example is provided below to illustrate the methods and techniques described herein. In particular, this example illustrates means to create an extended depth of focus while maintaining high image resolution in scanning fiber imaging system, such as a scanning fiber endoscope (SFE). Typically, an SFE has a single mode optical fiber that is driven in a spiral pattern to deliver illumination in a space-filling round area over the surface to be imaged. The optical system (objective lens system) between the scanning fiber tip and the tissue defines the image resolution in the SFE. The optical system is typically designed for high spatial resolution in the images, thus being having an undesirably short depth of focus or field.

To achieve extended depth of focus or field, the single optical fiber scanner is replaced with an opto-mechanical scanning cantilever that has more than one waveguide and more than one effective point source for the illumination. By varying the effective source point relative to the objective lens in a fixed optical system, the focal point is shifted at the illumination plane on the surface of a target area or object.

In this example, three or four single mode optical fibers made from silicon dioxide (quartz) material have the cladding etched from the standard 125 microns in outer diameter to approximately 10 to 50 microns in outer diameter, and in length from the free distal tip to about 2 to 8 mm proximally. The three or four optical fibers are held together (side by side) and their tips trimmed to make an optical smooth end-face with a carbon dioxide laser. The proximal ends of the optical fiber strands are pulled so the tips are not all flush or end at the same point at their free ends. Each end-face of the optical fibers is staggered by a small axial distance (e.g.,  less than 1 to 2 mm) to create separate and axially shifted or staggered illumination planes using a single objective lens system.

Once the geometry of the three or four parallel optical fibers has been established, the etched regions of the three or four fibers are bonded together using any one or a combination of the following techniques: (1) using carbon dioxide laser to weld the fibers together; (2) using heat to weld the fiber together; (3) using optical epoxy to bind the fibers together; (4) using adhesive or chemical to bind the fibers; and/or (5) using physical tubing that may be shrunk to hold the fibers together. The fused opto-mechanical system would be driven into a resonant vibratory mode in similar fashion as the SFE to produce a space-filling illumination. However, this illumination will produce three or four different planes of focus that can give three or four different high resolution images if the backscatter light is detected in a frame-sequential, scan-line-sequential, or even pixel-sequential manner. In this case, the same set of red, green, or blue optical detectors may be used for imaging from each of the three or four different illumination planes to generate an extended depth of field, high-resolution image of a surface with topographic relief. In a confocal arrangement, separate individual optical detectors of light (e.g. fluorescence) may be used to measure optical signals collected within the core of each optical fiber that was used to illuminate a particular focal plane.

Each illumination plane can have a very limited depth of focus or field of view, but in combination the resulting images of the target area can have the desired extended depth of focus at the highest resolution. For example, each of the three or four two-dimensional images resulting from the embodiment above may be computer processed to identify the regions or pixels within the image of highest focus. Knowing beforehand where the focal depth is for each illumination fiber, the regions (pixels) of highest focus may be combined in a three-dimensional mapping to the correct X and Y pixel location of the 2D image and the Z location of each of the three or four imaging planes. In some embodiments, the sharpest-focused portion of the composite image may come from only one of the illumination planes for a given Z location.

In the example, the cladding of the cantilevered optical fibers does not have to be etched first before being bound together. The etching procedure is proposed to simply save space for the microendoscopy application and create a multi-waveguide quartz cantilever of approximately the same overall diameter as our current 80 to 125 micron single optical fiber used within the micro-optical fiber scanner.

In the example, the end faces of the optical fibers may be cut and polished at an angle such as illustrated in FIG. 8 so that light emerging from an optical fiber tip does not strike an adjacent optical fiber. The angle may be approximately 8 degrees relative to the axis perpendicular to the optical core. The resulting light cone emitted from the angled end face may deviate approximately 12 degrees from the optical core. In various embodiments, the cut angle and the deviation angle may be more or less than 8 and 12 degrees, respectively.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for projecting a composite image to a target area, comprising:
scanning an optical fiber assembly in a scan pattern so as to provide illumination to the target area, the optical fiber assembly comprising a plurality of optical fibers optically coupled to an optical system to focus light from the optical fiber assembly and produce a plurality of focal planes located at different distances with respect to an optical axis in the optical system;
modulating the intensity of the provided light based on an image to create variation in light intensity across the target area; and
projecting, based at least in part on the illumination provided to the target area, a composite image based on the image onto the target area, the composite image having a depth of field spanning over a distance between the plurality of focal planes.

2. The method of claim 1, wherein the plurality of optical fibers are arranged in an axially staggered fashion.

3. The method of claim 1, wherein at least two of the plurality of optical fibers are coupled to each other.

4. The method of claim 1, wherein scanning the plurality of optical fibers includes actuating, by a scanner actuator, the distal portions of the plurality of optical fibers in a scan pattern.

5. The method of claim 4, wherein the optical system remains substantially stationary relative to the optical fiber assembly.

6. The method of claim 1, wherein projecting the composite image includes projecting a plurality of images respectively corresponding to the plurality of focal planes.

7. The method of claim 6, wherein each of the plurality of images are projected by one of the plurality of optical fibers.

8. The method of claim 6, wherein the plurality of images are projected simultaneously.

9. The method of claim 6, wherein the composite image is three-dimensional and the plurality of images are two-dimensional.

10. The method of claim 1, wherein at least some of the plurality of optical fibers have angled distal end-faces.

11. A system for projecting images onto a target area, comprising:
an optical fiber assembly comprising a plurality of optical fibers operable to provide illumination to the target area;
an optical system optically coupled with the optical fiber assembly, the optical system operable to focus illumination from optical fiber assembly to produce a plurality of focal planes located at different distances with respect to an optical axis in the optical system;
a scanner actuator coupled to the optical fiber assembly configured to actuate distal portions associated with the plurality of optical fibers to scan, either together or individually, in a scan pattern on the plurality of focal planes; and
one or more processors comprising a tangible medium, the tangible medium comprising instructions that when executed cause the one or more processors to project, based at least in part on the illumination provided to the target area, a 3-D composite image having a depth of field spanning over a distance between the plurality of focal planes.

12. The system of claim 11, wherein the plurality of optical fibers are arranged in an axially staggered fashion.

13. The system of claim 11, wherein at least two of the plurality of optical fibers are coupled to each other.

14. The system of claim 11, wherein scanning the plurality of optical fibers includes actuating, by a scanner actuator, the distal portions of the plurality of optical fibers in a scan pattern.

15. The system of claim 14, wherein the optical system remains substantially stationary relative to the optical fiber assembly.

16. The system of claim 11, wherein projecting the 3-D composite image includes projecting a plurality of images respectively corresponding to the plurality of focal planes.

17. The system of claim 16, wherein each of the plurality of images are projected by one of the plurality of optical fibers.

18. The system of claim 16, wherein the plurality of images are projected simultaneously.

19. The system of claim 16, wherein the plurality of images are two-dimensional.

20. The system of claim 11, wherein at least some of the plurality of optical fibers have angled distal end-faces.

* * * * *